United States Patent
Jorgensen et al.

(10) Patent No.: US 9,056,863 B2
(45) Date of Patent: Jun. 16, 2015

(54) SUBSTITUTED 2,3,5,9,9B-PENTAAZACYCLOPENTA[A]NAPHTHALENES AND USES THEREOF

(75) Inventors: Morten Jorgensen, Bagsværd (DK); Anne Techau Bruun, Hvidovre (DK); Lars Kyhn Rasmussen, Vanløse (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 14/343,402

(22) PCT Filed: Sep. 10, 2012

(86) PCT No.: PCT/EP2012/067639
§ 371 (c)(1),
(2), (4) Date: Apr. 23, 2014

(87) PCT Pub. No.: WO2013/034761
PCT Pub. Date: Mar. 14, 2013

(65) Prior Publication Data
US 2014/0235645 A1  Aug. 21, 2014

Related U.S. Application Data

(60) Provisional application No. 61/532,646, filed on Sep. 9, 2011.

(30) Foreign Application Priority Data

Sep. 9, 2011 (DK) .................... 2011 00685

(51) Int. Cl.
*A61K 31/4985* (2006.01)
*C07D 487/14* (2006.01)
*C07D 471/14* (2006.01)

(52) U.S. Cl.
CPC .................... *C07D 471/14* (2013.01)

(58) Field of Classification Search
CPC .................... A61K 31/4985; C07D 487/14
USPC ............................ 514/250; 544/346
See application file for complete search history.

(56) References Cited

FOREIGN PATENT DOCUMENTS

WO  2010/145668 A1  12/2010
WO  WO 2013/034761  *  3/2013

OTHER PUBLICATIONS

Jordan, V. C. Nature Reviews: Drug Discovery, 2, 2003, 205.*
Hackam, et al. JAMA, 296(14), 2006, 1731-1732.*
John Kehler et al., 2009, "Patented PDE10A inhibitors: novel compounds since 2007", Expert Opinion, 19 (12), pp. 1715-1725.
International Search Report and Written Opinion issued Dec. 17, 2012 in International Application No. PCT/EP2012/067639.

* cited by examiner

*Primary Examiner* — Douglas M Willis
(74) *Attorney, Agent, or Firm* — Mary Catherine Di Nunzio

(57) ABSTRACT

The present invention is directed to pyridine compounds of Formula (I). Separate aspects of the invention are directed to pharmaceutical compositions comprising said compounds and uses of the compounds as therapeutic agents treating neurological and psychiatric disorders.

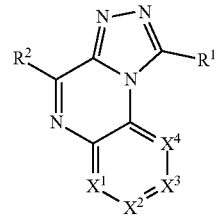

23 Claims, No Drawings

SUBSTITUTED 2,3,5,9,9B-PENTAAZACYCLO-PENTA[A]NAPHTHALENES AND USES THEREOF

FIELD OF THE INVENTION

The present invention is directed to compounds which are useful as therapeutic agents treating neurological and psychiatric disorders. Separate aspects of the invention are directed to pharmaceutical compositions comprising said compounds and uses thereof.

BACKGROUND ART

Cyclic-adenosine monophosphate (cAMP) and cyclic-guanosine monophosphate (cGMP) function as intracellular second messengers regulating an array of processes in neurons. Intracellular cAMP and cGMP are generated by adenyl and guanyl cyclases, and are degraded by cyclic nucleotide phosphodiesterases (PDEs). Intracellular levels of cAMP and cGMP are controlled by intracellular signaling, and stimulation/repression of adenyl and guanyl cyclases in response to GPCR activation is a well characterized way of controlling cyclic nucleotide concentrations (Antoni, *Front. Neuroendocrinol.* 2000, 21, 103-132).

Phosphodiesterase 2A (PDE2A) is a dual substrate enzyme with higher affinity for cGMP although it may metabolize either cAMP or cGMP depending on the tissue. cAMP is derived from adenosine triphosphate (ATP) and used for intracellular signal transduction in many different organisms, conveying the cAMP-dependent pathway. Although expressed in the periphery, the highest expression levels of PDE2A are in the brain. A recent immunohistochemical study demonstrated a consistent pattern of PDE2A expression in the brain across mammalian species including humans (Stephenson, et al. *J. Histochem. Cytochem.* 2009, 57, 933). The enzyme expression was shown to be prominent in regions associated with cognitive function and mood control, including the cortex, striatum, hippocampus, amygdala and the habenula.

The selective PDE2A inhibitor, Bay 60-7550, preferentially increases cGMP in primary neuronal cultures and hippocampal slices. Bay 60-7550 also increases long term potentiation (LTP) induction in rat hippocampal slices. Consistent with its biochemical and electrophysiological effects, Bay 60-7550 was found to be active in novel object and social recognition tasks (Boess, et al. *Neuropharmacology* 2004, 47, 1081). More recently, Bay 60-7550 was reported to reverse the deficit in object recognition produced by tryptophan depletion (van Donkelaar, et al. *Eur. J. Pharmacol.* 2008, 600, 98). These results are interesting in light of the PDE2 positive cells identified in the dorsal raphe, a region known to contain the cell bodies of the serotonergic neurons projecting to the forebrain (Stephenson, et al. *J. Histochem. Cytochem.* 2009, 57, 933). A similar study in aged rats demonstrated that the beneficial effect of Bay 60-7550 on object recognition could be reversed by a neuronal nitric oxide synthase (nNOS) inhibitor, suggesting that the effects of PDE2A inhibition in the central nervous system (CNS) are due to alterations in the levels of cGMP (Domek-Lopacinska and Strosznajder *Brain Res.* 2008, 1216, 68).

Recent studies indicate that PDE2A inhibition may also efficacy in the treatment of anxiety states (Masood, et al. *J. Pharmacol. Exp. Ther.* 2008, 326, 369; and Masood, et al. *J. Pharmacol. Exp. Ther.* 2009, 331, 699). Induction of oxidative stress in mice by depletion of central glutathione levels with buthionine sulfoximine (BSO) results in an increase in a number of anxiety-like behaviours assessed by open field time and the elevated plus maze assays. These effects were reversed by treatment with Bay 60-7550. Increased cGMP signaling, either by administration of the PDE2 inhibitors Bay 60-7550 or ND7001, or the NO donor detanonoate, antagonized the anxiogenic effects of restraint stress on behaviour in the elevated plus-maze, hole-board, and open-field tests, well established procedures for the evaluation of potential anxiolytics. These drugs also produced anxiolytic effects on behavior in non-stressed mice in the elevated plus-maze and hole-board tests. By contrast, administration of an NOS inhibitor, which reduces cGMP signaling, produced anxiogenic effects similar to restraint stress.

Phosphodiesterase 10A (PDE10A) is another dual-specificity enzyme that can convert both cAMP to AMP and cGMP to GMP (Soderling, et al. *Proc. Natl. Acad. Sci.* 1999, 96, 7071). PDE10A hydrolyses both cAMP and cGMP having a higher affinity for cAMP. PDE10A is expressed in the neurons in the striatum, n. accumbens and in the olfactory tubercle (Seeger, et al. Brain Research, 2003, 985, 113-126) and the thalamus, hippocampus, frontal cortex and olfactory tubercle (Menniti et al., William Harvey Research Conference, Porto, December, 2001). All these brain areas are described to participate in the pathomechanism of schizophrenia (Lapiz, et al. *Neurosci Behav Physiol* 2003, 33, 13) so that the location of the enzyme indicates a predominate role in the pathomechanism of psychosis. In the striatum, PDE10A is predominately found in the medium spiny neurons and they are primarily associated to the postsynaptic membranes of these neurons (Xie et al., *Neuroscience* 2006, 139, 597). In this location PDE10A may have an important influence on the signal cascade induced by dopaminergic and glutamatergic input on the medium spiny neurons two neurotransmitter systems playing a predominate role in the pathomechanism of psychosis.

Psychotic patients have been shown to have a dysfunction of cGMP and cAMP levels and their downstream substrates (Muly, *Psychopharmacol Bull* 2002, 36, 92). Additionally, haloperidol treatment has been associated with increased cAMP and cGMP levels in rats and patients, respectively (Leveque et al., *J. Neurosci.* 2000, 20, 4011). As PDE10A hydrolyses both cAMP and cGMP, an inhibition of PDE10A would also induce an increase of cAMP and cGMP and thereby have a similar effect on cyclic nucleotide levels as haloperidol. The antipsychotic potential of PDE 10A inhibitors is further supported by studies of Kostowski et al. (*Pharmacol Biochem Behav* 1976, 5, 15) who showed that papaverine, a moderately selective PDE10A inhibitor, reduces apomorphine-induced stereotypies in rats, an animal model of psychosis, and increases haloperidol-induced catalepsy in rats while concurrently reducing dopamine concentration in rat brain, activities that are also seen with classical antipsychotics. In addition to classical antipsychotics which mainly ameliorate the positive symptoms of psychosis, PDE10A also bears the potential to improve the negative and cognitive symptoms of psychosis.

Focusing on the dopaminergic input on the medium spiny neurons, PDE10A inhibitors by up-regulating cAMP and cGMP levels act as D1 agonists and D2 antagonists because the activation of Gs-protein coupled dopamine D1 receptor increases intracellular cAMP, whereas the activation of the Gi-protein coupled dopamine D2 receptor decreases intracellular cAMP levels through inhibition of adenylyl cyclase activity. Elevated intracellular cAMP levels mediated by D1 receptor signalling seems to modulate a series of neuronal processes responsible for working memory in the prefrontal cortex (Sawaguchi, *Parkinsonism Relat. Disord.* 2000, 7, 9), and it is reported that D1 receptor activation may improve working memory deficits in schizophrenic patients (Castner, et al., *Science* 2000, 287, 2020).

Further indication of an effect of PDE10A inhibition on negative symptoms of psychosis was given by Rodefer et al. (*Eur. J Neurosci* 2005, 21, 1070) who could show that papaverine reverses attentional set-shifting deficits induced by subchronic administration of phencyclidine, an NMDA antagonist, in rats. Attentional deficits including an impairment of shifting attention to novel stimuli belongs to the negative symptoms of schizophrenia. In the study the attentional deficits were induced by administering phencyclidine for 7 days followed by a washout period. The PDE10A inhibitor papaverine was able to reverse the enduring deficits induced by the subchronic treatment.

These convergent findings indicate that the inhibition of PDE2A and/or PDE10A may be therapeutic targets for the treatment of certain neurological and psychiatric disorders. Accordingly, the present invention relates to pyridine containing triazolopyrazines, to their preparation, to their medical use and to medicaments comprising them.

SUMMARY OF THE INVENTION

An objective of the present invention is to provide compounds that inhibit PDE2A and/or PDE10A. Accordingly, the present invention relates to compounds of formula I

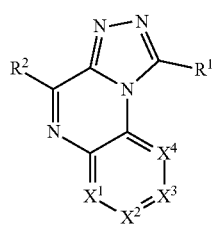

Formula I wherein each $X^1$, $X^2$, $X^3$ and $X^4$ is independently N or $CR^3$ provided one X is N and the remaining X are each independently $CR^3$;
wherein $R^1$ is $C_1$-$C_6$ alkyl, $C_3$-$C_6$ cycloalkyl, tetrahydropyranyl, benzyl, phenyl and pyridyl, in which the benzyl, phenyl and pyridyl is optionally substituted with one or more halogen, CN, $C_1$-$C_4$ alkyl/fluoroalkyl or $C_1$-$C_4$ alkoxy/fluoroalkoxy;
wherein $R^2$ is $C_1$-$C_4$ alkyl or $C_3$-$C_6$ cycloalkyl; and
wherein $R^3$ is hydrogen, halogen, CN, —$CO_2H$, —CON(H or $C_1$-$C_4$ alkyl)$_2$, CHO, $C_1$-$C_4$ alkyl/fluoroalkyl, a cyclic amino containing heterocycle, $C_2$-$C_4$ alkenyl, $C_2$-$C_4$ alkenyl or $C_1$-$C_4$ alkoxy/fluoroalkoxy; or a pharmaceutically acceptable salt thereof.

In separate aspects of the invention, the compound is selected from one of the exemplified compounds of formula I.

The present invention provides a pharmaceutical composition comprising a therapeutically effective amount of a compound of formula I and a pharmaceutically acceptable carrier.

Methods of treating a subject suffering from anxiety, a cognitive disorder or schizophrenia comprising administering a therapeutically effective amount of a compound of formula I are provided.

The present invention further provides uses of a compound of formula I in the manufacture of a medicament for treating anxiety, a cognitive disorder or schizophrenia.

Another aspect of the present invention provides a compound for use in treating anxiety, a cognitive disorder or schizophrenia.

DETAILED DESCRIPTION OF THE INVENTION

The present invention is based on the discovery of the compounds of formula I which inhibit PDE2A and/or PDE10A, and as such, are useful for the treatment of certain neurological and psychiatric disorders. Particular aspects of the invention are explained in greater detail below but this description is not intended to be a detailed catalog of all the different ways in which the invention may be implemented, or all the features that may be added to the instant invention. Hence, the following specification is intended to illustrate some embodiments of the invention, and not to exhaustively specify all permutations, combinations and variations thereof.

It is understood by those practicing the art that compounds can exist in tautomeric forms. When any reference in this application to one of the specified tautomers is given, it is understood to encompass its tautomeric forms and mixtures thereof.

The subject invention is directed to compounds of formula I as defined in the summary of the invention, pharmaceutical compositions and uses thereof.

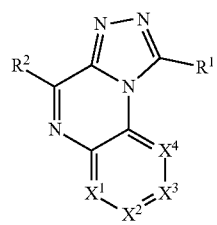

Formula I

In one embodiment, $R^2$ is $C_1$-$C_4$ alkyl. In one embodiment, $R^2$ is methyl.
In one embodiment, $R^2$ is $C_3$-$C_6$ cycloalkyl.
In one embodiment, $R^1$ is $C_1$-$C_4$ alkyl.
In one embodiment, $R^1$ is $C_3$-$C_6$ cycloalkyl.
In one embodiment, $R^1$ is tetrahydropyranyl.
In one embodiment, $R^1$ is benzyl optionally substituted with one or two F, Cl or $C_1$-$C_3$ alkyl.
In one embodiment, $R^1$ is phenyl optionally substituted with one or two F, Cl or $C_1$-$C_3$ alkyl.
In one embodiment, $R^1$ is pyridyl optionally substituted with one or two F, Cl or $C_1$-$C_3$ alkyl.
In one embodiment, $R^1$ is phenyl substituted with one or two F, Cl or $C_1$-$C_3$ alkyl.
In one embodiment, $X^1$ is N. In one embodiment, $X^2$ is N. In one embodiment, $X^3$ is N. In one embodiment, $X^4$ is N.
In one embodiment, $R^3$ is hydrogen. In one embodiment, $R^3$ is halogen or CHO.
In one embodiment, $R^3$ is $C_1$-$C_4$ alkyl or $C_1$-$C_4$ alkoxy.
In one embodiment, $R^3$ is $C_2$-$C_4$ alkenyl or $C_2$-$C_4$ alkenyl.
In one embodiment, $R^3$ is a cyclic amino containing heterocycle.
In one embodiment, $R^3$ is CN, —$CO_2H$ or —CON(H or $C_1$-$C_4$ alkyl)$_2$.

Racemic forms may be resolved into the optical antipodes by known methods, for example, by separation of diastereomeric salts thereof with an optically active acid, and liberating the optically active amine compound by treatment with a base. Separation of such diastereomeric salts can be achieved, e.g. by fractional crystallization. The optically active acids suitable for this purpose may include, but are not limited to d- or l-tartaric, mandelic or camphorsulfonic acids. Another method for resolving racemates into the optical antipodes is based upon chromatography on an optically active matrix. The compounds of the present invention may also be resolved by the formation and chromatographic separation of diastereomeric derivatives from chiral derivatizing reagents, such as, chiral alkylating or acylating reagents, followed by cleavage of the chiral auxiliary. Any of the above methods may be applied either to resolve the optical antipodes of the compounds of the invention per se or to resolve the optical antipodes of synthetic intermediates, which can then be converted by methods described herein into the optically resolved final products which are the compounds of the invention.

Additional methods for the resolution of optical isomers, known to those skilled in the art, may be used. Such methods include those discussed by J. Jaques, A. Collet and S. Wilen in Enantiomers, Racemates, and Resolutions, John Wiley and Sons, New York, 1981. Optically active compounds can also be prepared from optically active starting materials.

DEFINITIONS

As used herein, the term "$C_1$-$C_6$ alkyl" refers to a straight chained or branched saturated hydrocarbon having from one to six carbon atoms inclusive. Examples include, but are not limited to, methyl, ethyl, 1-propyl, 2-propyl, 1-butyl, 2-butyl, 2-methyl-2-propyl, 2-methyl-1-propyl, n-pentyl and n-hexyl. Similarly, the term "straight chained or branched $C_1$-$C_4$ alkyl" refers to a saturated hydrocarbon having from one to four carbon atoms. Examples include methyl, ethyl and n-propyl.

Likewise, the term "$C_1$-$C_4$ alkoxy" refers to a straight chained or branched saturated oxygen containing hydrocarbon group having from one to four carbon atoms with the open valency on the oxygen. Examples include, but are not limited to, methoxy, ethoxy, n-butoxy, and t-butoxy.

The term "$C_1$-$C_6$ fluoroalkyl" refers to a straight chained or branched saturated hydrocarbon having from one to six carbon atoms inclusive substituted with one or more fluorine atoms. Examples include trifluoromethyl, pentafluoroethyl, 1-fluoroethyl, monofluoromethyl, difluoromethyl, 1,2-difluoroethyl and 3,4 difluorohexyl. Similarly, the term "straight chained or branched $C_1$-$C_4$ fluoroalkoxy" refers to a saturated hydrocarbon having from one to four carbon atoms substituted with one or more fluorine atoms with the open valency on the oxygen.

The term "halogen" refers to fluorine, chlorine, bromine and iodine.

The term "$C_2$-$C_4$-alkenyl" refers to a branched or unbranched alkenyl group having from two to four carbon atoms and one double bond, which includes ethenyl, propenyl, and butenyl. The term "$C_2$-$C_4$-alkynyl" shall mean a branched or unbranched alkynyl group having from two to four carbon atoms and one triple bond, which includes ethynyl, propynyl and butynyl.

For the purposes of this invention, the term "cyclic amino containing heterocycle" refers to azetidine, pyrrolidine, piperidine, piperazine and morpholine. The "cyclic amino containing heterocycle" is optionally substituted with one or more straight chained or branched $C_1$-$C_4$ alkyl.

The term "CON(H or $C_1$-$C_4$ alkyl)$_2$" refers to an amido group in which the substituents off the amido moiety are each independently selected from the group consisting of H or $C_1$-$C_4$ alkyl. Examples include —CONH$_2$, —CONHCH$_3$, —CON(CH$_3$)$_2$ and —CON(CH$_3$)CH$_2$CH$_3$.

The term "treatment" or "treating" as used herein means ameliorating or reversing the progress or severity of a disease or disorder, or ameliorating or reversing one or more symptoms or side effects of such disease or disorder. "Treatment" or "treating", as used herein, also means to inhibit or block, as in retard, arrest, restrain, impede or obstruct, the progress of a system, condition or state of a disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of a disease or disorder state, amelioration or palliation of a disease or disorder state, and remission of a disease or disorder, whether partial or total, detectable or undetectable.

As used herein, the phrase "effective amount" when applied to a compound of the invention, is intended to denote an amount sufficient to cause an intended biological effect.

The phrase "therapeutically effective amount" when applied to a compound of the invention is intended to denote an amount of the compound that is sufficient to ameliorate, palliate, stabilize, reverse, slow or delay the progression of a disorder or disease state, or of a symptom of the disorder or disease. In an embodiment, the method of the present invention provides for administration of combinations of compounds. In such instances, the "effective amount" is the amount of the combination sufficient to cause the intended biological effect.

Pharmaceutically Acceptable Salts

The present invention also comprises salts of the present compounds, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines (for example, 8-bromotheophylline and the like). Further examples of pharmaceutically acceptable inorganic or organic acid addition salts include the pharmaceutically acceptable salts listed in S. M. Berge, et al., J. Pharm. Sci., 1977, 66, 2.

Furthermore, the compounds of this invention may exist in unsolvated as well as in solvated forms with pharmaceutically acceptable solvents such as water, ethanol and the like.

Pharmaceutical Compositions

The present invention further provides a pharmaceutical composition comprising a therapeutically effective amount of a compound of formula I and a pharmaceutically acceptable carrier. The present invention also provides a pharmaceutical composition comprising a therapeutically effective amount of one of the specific compounds disclosed in the Experimental Section and a pharmaceutically acceptable carrier.

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use.

Oral dosages are usually administered in one or more dosages, typically, one to three dosages per day. The exact dosage will depend upon the frequency and mode of administration, the sex, age, weight and general condition of the subject treated, the nature and severity of the condition treated and any concomitant diseases to be treated and other factors evident to those skilled in the art. The formulations may also be presented in a unit dosage form by methods known to those skilled in the art. For illustrative purposes, a unit dosage form for oral administration may contain from about 0.01 to about 1000 mg, from about 0.05 to about 500 mg, or from about 0.5 to about 200 mg.

The compounds of this invention are generally utilized as the free substance or as a pharmaceutically acceptable salt thereof. One example is an acid addition salt of a compound having the utility of a free base. When a compound of formula I contains a free base such salts are prepared in a conventional manner by treating a solution or suspension of a free base of formula I with a molar equivalent of a pharmaceutically acceptable acid. Representative examples of suitable organic and inorganic acids are described above.

For parenteral administration, solutions of the compounds of formula I in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The compounds of formula I may be readily incorporated into known sterile aqueous media using standard techniques known to those skilled in the art.

Suitable pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compounds of formula I and a pharmaceutically acceptable carrier are then readily administered in a variety of dosage forms suitable for the disclosed routes of administration. The formulations may conveniently be presented in unit dosage form by methods known in the art of pharmacy.

If a solid carrier is used for oral administration, the preparation may be tabletted, placed in a hard gelatin capsule in powder or pellet form or it may be in the form of a troche or lozenge. The amount of solid carrier will vary widely but will range from about 25 mg to about 1 g per dosage unit. If a liquid carrier is used, the preparation may be in the form of a syrup, emulsion, soft gelatin capsule or sterile injectable liquid such as an aqueous or non-aqueous liquid suspension or solution.

Therapeutic Uses

Methods of treating a subject suffering from anxiety, a cognitive disorder or schizophrenia comprising administering a therapeutically effective amount of a compound of formula I are provided in this invention.

The present invention further provides uses of a compound of formula I in the manufacture of a medicament for treating an anxiety disorder, a cognitive disorder or schizophrenia. Another aspect of the present invention provides a compound for use in treating an anxiety disorder, a cognitive disorder or schizophrenia. The present invention provides a method of treating anxiety, a cognitive disorder or schizophrenia comprising administering a therapeutically effective amount of a compound of formula I or a pharmaceutically acceptable salt thereof.

The present invention provides a method of treating an anxiety disorder is selected from anxiety; panic disorder; agoraphobia; a specific phobia; social phobia; obsessive-compulsive disorder; post-traumatic stress disorder; acute stress disorder; and generalized anxiety disorder.

The present invention further provides a method of treating a subject suffering from a cognition disorder comprising administering to the subject a therapeutically effective amount of a compound of formula I. Examples of cognition disorders that can be treated according to the present invention include, but are not limited to, Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; and age-related cognitive decline.

This invention also provides a method of treating a movement disorder comprising administering to the subject a therapeutically effective amount of a compound of formula I. Examples of movement disorders that can be treated according to the present invention include, but are not limited to, Huntington's disease and dyskinesia associated with dopamine agonist therapy. This invention further provides a method of treating a movement disorder selected from Parkinson's disease and restless leg syndrome, which comprises administering to the subject a therapeutically effective amount of a compound of formula I.

The present invention provides a method of treating schizophrenia, for example of the paranoid, disorganized, catatonic, undifferentiated, or residual type; schizophreniform disorder; schizoaffective disorder, for example of the delusional type or the depressive type; delusional disorder; substance-induced psychotic disorder, for example psychosis induced by alcohol, amphetamine, cannabis, cocaine, hallucinogens, inhalants, opioids, or phencyclidine; personality disorder of the paranoid type; and personality disorder of the schizoid type; and wherein the drug addiction is an alcohol, amphetamine, cocaine, or opiate addiction.

Experimental Section

The compounds of formula I can be prepared by the methods outlined in the following methods and in the examples. In the methods below, it is possible to make use of variants or modifications, which are themselves known to chemists skilled in the art or could be apparent to the person of ordinary skill in this art. Furthermore, other methods for preparing compounds of the invention will be readily apparent to the person skilled in the art in light of the following reaction schemes and examples. For example, the methods describe the use of selective protecting groups during the synthesis of the compounds of the invention. One skilled in the art would be able to select the appropriate protecting group for a particular reaction. Methods for protection and deprotection of such groups are well known in the art, and may be found in T. Green, et al., Protective Groups in Organic Synthesis, 1991, $2^{nd}$ Edition, John Wiley & Sons, New York.

Abbreviations and Chemicals Used

AcOH=acetic acid (e.g. Sigma-Aldrich 242853). Acetonitrile (e.g. Aldrich 271004). APPI=atmospheric pressure photo ionization. Aq=aqueous. Brine=saturated aq solution of sodium chloride (e.g. Aldrich S7653). Boc$_2$O=di-tert-butyl dicarbonate (e.g. Aldrich 361941). 2-Chloro benzoic acid (e.g. Aldrich 135577). 3-Chloro benzoic acid (e.g. Fluka 23530). 3-Chloro benzoyl chloride (e.g. Aldrich C26801). Chloroform (e.g. Sigma-Aldrich C2432). 2-Chloro-6-methyl-benzoic acid (e.g. Lancaster X18348 or Matrix 002794). 2-Chloro-6-methyl-benzoyl chloride (e.g. Fluorochem 38160 or Betapharm 15-47106). DBU=1,8-Diazabicyclo [5.4.0]undec-7-ene (e.g. Aldrich 139009). DCM=methylene chloride/dicholormethane (e.g. Aldrich 270997). 2,6-dichloro-benzoic acid (e.g. Aldrich D57450). 2,3-Diamino pyridine (e.g. Aldrich 125857). 3,4-Diamino pyridine (e.g. Aldrich D7148). Diethyl ether (e.g. Sigma-Aldrich 346136). DMAP=4-(dimethylamino)pyridine (e.g. Aldrich 522805). 2,6-Dimethyl benzoyl chloride (e.g. Fluorochem 017526 or ABCR AB 173115). DMF=dimethyl formamide (e.g. Sigma-Aldrich 227056). DIPEA=di-iso-propyl ethyl amine (e.g. Aldrich 387649). ELS=evaporative light scattering. Ethanol (e.g. Sigma-Aldrich 459844). Ethyl pyruvate (e.g. Fluka 15960). EtOAc=ethyl acetate (e.g. Fluka 34972). 2-Fluoro-3-nitro-pyridine (e.g. Fluorochem 03250 or Matrix 018339). h=hour(s). 4M HCl in 1,4-dioxane (e.g. Sigma-Aldrich 345547). Heptanes (e.g. Sigma-Aldrich 730491). HPLC=high performance liquid chromatography. 30% aq hydrogen peroxide (e.g. Sigma-Aldrich 216763). Hydrazine hydrate (e.g. Sigma-Aldrich 225819). Iron powder (e.g. Aldrich 12310). LC=liquid chromatography. LC/MS=liquid chromatography/mass spectrometry. 4M=4 molar solution. Methanol (e.g. Sigma-Aldrich 34860). MTBE=methyl tert-butyl ether (e.g. Sigma-Aldrich 306975). MW=microwave. MW conditions=reactions performed in sealed tubes using a Biotage Initiator instrument or a CEM Explorer-48 instrument. Na$_2$CO$_3$ (e.g. Sigma-Aldrich S7795). NaHCO$_3$ (e.g. Sigma-Aldrich S6014). NaOH (e.g. Sigma-Aldrich S5881). Na$_2$SO$_4$ (e.g. Sigma-Aldrich 238597). 3-Nitro-pyridin-4-ylamine (e.g. Aldrich 646962). 10% Palladium on charcoal (e.g. Aldrich 75990). PDA=photo diode array. Pd(DPPF) Cl$_2$=[1,1'-Bis(diphenylphosphino)ferrocene]dichloropalladium(II) (e.g. Aldrich 697230) Pd(DPPF)Cl$_2$-DCM complex=[1,1'-Bis(diphenylphosphino)ferrocene] dichloropalladium(II), complex with dichloromethane (e.g. Aldrich 379670). Pentane (e.g. Sigma-Aldrich 236705). PhPOCl$_2$=phenylphosphonic dichloride (e.g. Aldrich 389560). POCl$_3$=phosphoryl chloride (e.g. Aldrich 262099). PyBroP=benzotriazol-1-yl-oxytripyrrolidinophosphonium hexafluorophosphate (e.g. Fluka 12809). Racemic alanine (e.g. Sigma A7502). RT=retention time. Sat=saturated. T=time. Tf$_2$O=Trifluoromethanesulfonic anhydride (e.g. Aldrich 176176). TLC=thin layer chromatography. Et$_3$N=triethylamine (e.g. Sigma-Aldrich T0886).

LC/MS Method 131: LC/MS were run on a Sciex API150EX equipped with APPI-source operating in positive ion mode. The HPLC consisted of Shimadzu LC10-ADvp LC pumps, SPD-M20A PDA detector (operating at 254 nM) and SCL-10A system controller. Autosampler was Gilson 215, Column oven was a Jones Chromatography 7990R and ELS detector was a Sedere Sedex 85. LC-conditions: The column was a Waters Symmetry C-18, 4.6×30 mm, 3.5 micom operating at 60° C. with 3.0 mL/min of a binary gradient consisting of water+0.05% TFA (A) and methanol+0.05% TFA. Gradient: 0.01 min. 17% B; 0.27 min 28% B; 0.53 min 39% B; 0.80 min 50% B; 1.07 min 59% B; 1.34 min 68% B; 1.60 min 78% B; 1.87 min 86% B; 2.14 min 93% B; 2.38 min 100% B; 2.40 min 17% B; 2.80 min 7% B; Total run time: 2.8 min.

LC/MS Method 132: same hardware as LC/MS method 131. LC-conditions: The column was a Waters Symmetry C-18, 4.6×30 mm, 3.5 microm operating at 60° C. with 2.5 mL/min of a binary gradient consisting of water+0.05% TFA (A) and methanol+0.05% TFA. Gradient: 0.01 min 5% B; 2.38 min 100% B; 2.40 min 5% B; 2.80 min 5% B. Total run time: 2.8 min.

Method 550: LC-MS were run on Waters Aquity UPLC-MS consisting of Waters Aquity including column mamager, binary solvent manager, sample organizer, PDA detector (operating at 254 nM), ELS detector, and TQ-MS equipped with APPI-source operating in positive ion mode. LC-conditions: The column was Acquity UPLC BEH C18 1.7 µm; 2.1×50 mm operating at 60° C. with 1.2 ml/min of a binary gradient consisting of water+0.05% trifluoroacetic acid (A) and acetonitrile+5% water+0.05% trifluoroacetic acid. Gradient: 0.00 min 10% B; 1.00 min 100% B; 1.01 min 10% B; 1.15 min 10% B. Total run time: 1.15 min

| Methods WXV-AB01 and WXV-AB10 and WXF-CD05 | | |
|---|---|---|
| Equipment | Agilent 1100 LCMS system with ELS Detector [method WXF-CD05 Agilent 1200 LCMS system with ELS | |
| | Pump | G1311A |
| | Degasser | G1379A |
| | Well-plate Autosampler | G1367A |
| | Column Oven | G1316A |
| | DAD | G1315B |
| | MSD | G1946C or G1956A |
| | ELSD | Alltech ELSD 800 |
| Column | YMC ODS-AQ | |
| | Particle size | 5 micrometer |
| | Pore size | 12 nm |
| | Dimension | 50 * 2.0 mm ID |
| Injection volume | 2 microL | |
| Column temperature | 50° C. | |
| Flow | 0.8 mL/min | |
| Mobile phases | A | 0.1% TFA in water |
| | B | 0.05% TFA in acetonitrile |
| | Total run time | 4.5 min (WXV-AB01 and WXF-CD05) |
| | Gradient | linear |

-continued

Methods WXV-AB01 and WXV-AB10 and WXF-CD05

| UV Detection | Wavelength | 254 nm |
| ELSD Detection | Temperature: | 50° C. |
| | Gas Pressure: | 3.2 bar |

| | Time | Gradient |
| --- | --- | --- |
| WXE-AB01 | 0 min | 99% A 1% B |
| | 3.4 min | 100% B |
| | 4 min | 100% B |
| | 4.01 min | 99% A 1% B |
| | 4.5 min | 99% A 1% B |
| WXE-AB10 | 0 min | 90% A 10% B |
| | 3.4 min | 100% B |
| | 4 min | 100% B |
| | 4.5 min | 90% A 10% B |
| WXV-AB05 | 0 min | 95% A 5% B |
| | 3.5 min | 5% A 95% B |
| | 3.55 min | 95% A 5% B |
| | 4.5 min | 95% A 5% B |

General Methods a suitable solvent like methylene chloride (DCM) to form the corresponding hydrazones. Subsequent addition of a suitable oxidant affords the compounds of the invention for example under the conditions reported by Sadana et al (A. K. Sadana, Y. Mirza, K. R. Aneja, O. Prakash *European Journal of Medicinal Chemistry* 2003, 38, 533) in which the oxidant is iodobenzene diacetate (PhI(OAc)$_2$). Alternatively it is possible to use the procedure reported by Mogilaiah et al (K. Mogilaiah, T. Kumara Swamy, K. Shiva Kumar *J. Heterocyclic Chem.* 2009, 46, 124) in which the intermediate hydrazones are cyclized oxidatively by treatment with chloramine-T.

Method 3 involves the displacement by hydrazine of X in compounds III wherein X is either a chlorine atom or another leaving group such as the phosphonium species drawn in the reaction scheme. The reaction typically occurs with hydrazine hydrate in a suitable solvent such as ethanol at elevated temperature. The preparations of IIc and IId are examples of method 3.

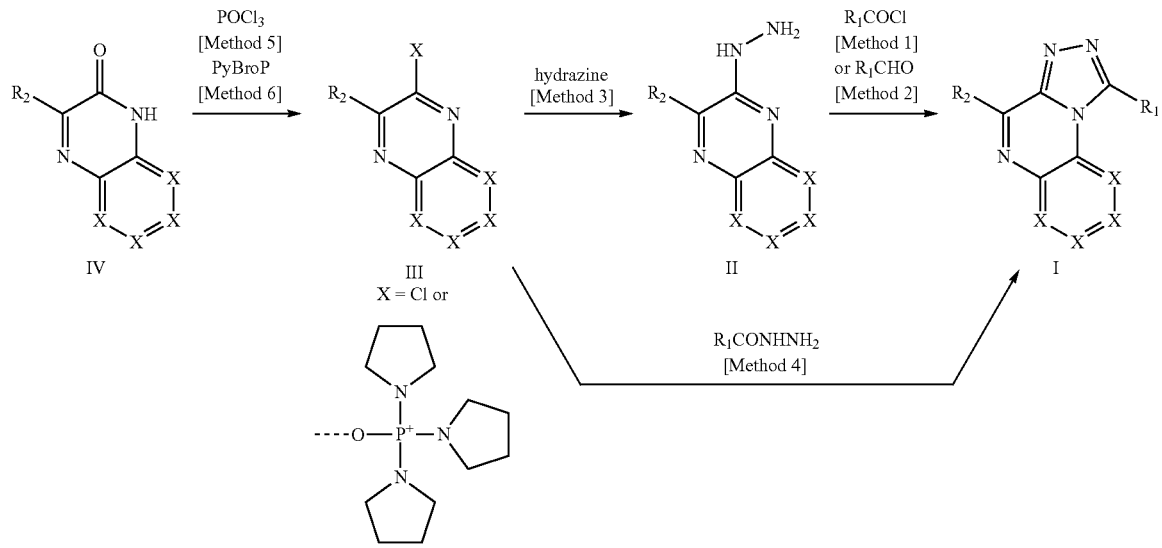

In brief, the compounds of the invention I can be prepared from hydrazines II under the conditions described as method 1 or method 2, respectively. Hydrazines II can be prepared from compounds III under the conditions described as method 3. In some cases, it is also possible to convert III directly to I using method 4. Precursors III can be obtained from lactams IV using either method 5 or method 6.

Method 1 consists of the treatment of hydrazines II with the appropriate acid chloride R$_1$COCl in a suitable solvent such as acetonitrile at elevated temperature. Sometimes it can be an advantage to add POCl$_3$ or PhPOCl$_2$. The acid chloride can be prepared in situ from the corresponding acid by the addition of POCl$_3$. Alternatively, the hydrazine II is reacted with R$_1$CO$_2$H and PyBroP to afford the corresponding hydrazide which is subsequently treated with PhPOCl$_2$ and base in two steps to afford the compounds of the invention as described for example Ia1.

Method 2 is an alternative to method 1 in which the hydrazine II is condensed with the appropriate aldehyde R$_1$CHO in Method 4 is the direct conversion of compounds III to the compounds of the invention I by reaction with the appropriate acid hydrazide R$_1$CONHNH$_2$ in a suitable solvent such as acetonitrile at elevated temperatures as described for example Id1.

Method 5 is the conversion of lactams IV to compounds III wherein X is a chlorine atom by heating the substrate in excess phosphoryl chloride as described for IId; sometimes it can be an advantage to add a suitable base such as triethyl amine or di-iso-propyl ethyl amine (DIPEA).

Method 6 is the treatment of lactams IV with benzotriazol-1-yl-oxytripyrrolidino-phosphonium hexafluorophosphate (PyBroP) or a similar peptide coupling agent in the presence of a suitable base such as DIPEA to provide compounds III wherein X is the phosphonium species drawn in the reaction scheme. This method is known for other lactams in the literature (T. D. Ashton, P. J. Scammells *Australian Journal of Chemistry* 2008, 61, 49). The preparation of IIa is an example of method 6.

Preparation of Intermediates

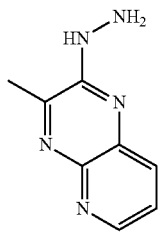

(3-Methyl-pyrido[2,3-b]pyrazin-2-yl)-hydrazine (IIa). A mixture of 2-fluoro-3-nitro-pyridine (12 g), Et$_3$N (30 mL), and racemic alanine (11.87 g) was refluxed in methanol (200 mL) overnight. The mixture was cooled to ambient temperature and the filtrate was concentrated in vacuo. The residue was partitioned between DCM and water. The organic layer was dried over Na$_2$CO$_3$, filtered, and concentrated in vacuo to afford 2-(3-nitro-pyridin-2-ylamino)-propionic acid (7.8 g). This material was dissolved in AcOH (50 mL) and iron (8.2 g) was added. The mixture was refluxed for 1.5 h. After cooling to ambient temperature, the mixture was filtered, and the filtrate was concentrated in vacuo. The residue was washed with water and dried to afford 3-methyl-3,4-dihydro-1H-pyrido[2,3-b]pyrazin-2-one (1.4 g). This material was mixed with 5% aq NaOH (92 mL) and water (18 mL) before 30% aq hydrogen peroxide (9.2 mL) was added. The mixture was stirred at 60° C. for 10 h. After cooling to ambient temperature the pH was adjusted to neutral to precipitate 3-methyl-1H-pyrido[2,3-b]pyrazin-2-one (1.2 g). This material was dissolved in DMF (10 mL) and treated with PyBroP (4.6 g) and DIPEA (1.6 mL) at ambient temperature of 16 h. The precipitated white solid was filtered off, washed with ethanol and dried to afford 2-(benzotriazol-1-yloxy)-3-methyl-pyrido[2,3-b]pyrazine (0.4 g). This material (0.4 g) and hydrazine hydrate (0.5 mL) were refluxed in ethanol (5 mL) for 10 min. After cooling to ambient temperature, the precipitated white solid was filtered off, washed with ethanol and dried to afford give IIa (0.2 g) sufficiently pure for the next step.

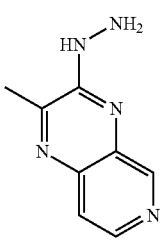

(3-Methyl-pyrido[2,3-b]pyrazin-2-yl)-hydrazine (IIc). A mixture of 3,4-diamino pyridine (10 g) and ethyl pyruvate (53 g) in chloroform (100 mL) was stirred at ambient temperature overnight. The precipitated solid was filtered off, washed with DCM, and dried to afford 2-methyl-4H-pyrido[3,4-b]pyrazin-3-one (14 g) as a yellowish solid. 2 g of this material was suspended in DMF (10 mL) and treated with PyBroP (6 g) and DIPEA (3.3 mL,) at ambient temperature overnight. The precipitated solid was filtered off, washed with ethanol, and dried to afford 3-(benzotriazol-1-yloxy)-2-methyl-pyrido[3,4-b]pyrazine (1.7 g) as a white solid. This material was suspended in ethanol (50 mL), hydrazine hydrate was added, and resulting mixture was heated at 85° C. for 15 min. The solid was filtered off, washed with ethanol, and dried to afford IIc (0.95 g) as a yellow solid sufficiently pure for the next step.

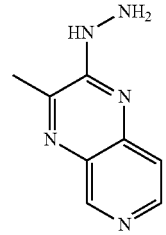

(3-Methyl-pyrido[3,4-b]pyrazin-2-yl)-hydrazine (IIb). To a suspension of 3-nitro-pyridin-4-ylamine (15 g) in DCM (250 mL) was added triethyl amine (30 mL), Boc$_2$O (23.5 g) and DMAP (1.31 g). The mixture was stirred at ambient temperature for 2 days. The solid was filtered off, and the filtrate was concentrated in vacuo. The residue was washed with MTBE. The yellow crystal was collected to afford (3-nitro-pyridin-4-yl)-carbamic acid tert-butyl ester (17 g). This material and ethyl pyruvate (100 mL) were dissolved in ethanol (150 mL) and treated with hydrogen gas (50 psi) in the presence of 10% palladium on charcoal (3 g) at 50° C. for two days. The catalyst was filtered off, and the filtrate was concentrated in vacuo. The residue was purified by chromatography on silica (eluent: pentane/EtOAc 10:1→2:1) to afford 2-(4-tert-butoxycarbonylamino-pyridin-3-ylamino)-propionic acid ethyl ester (5 g) as a yellow solid. A larger sample of this compound prepared in a similar manner (9 g) was stirred in 4M HCl in 1,4-dioxane (40 mL) at ambient temperature for 5 h. The precipitated solid was filtered off, washed with MTBE, and dried. The filtrate was concentrated to dryness, washed with MTBE, and dried to afford a second crop of the product. Total yield of 3-methyl-3,4-dihydro-1H-pyrido[3,4-b]pyrazin-2-one hydrochloride (5 g) as a white solid. 2.2 g of this material was suspended in water (20 mL) and treated with 30% aq hydrogen peroxide (1.2 mL) and NaOH (to adjust pH to 7-8). The mixture was stirred at 75° C. for 2 days. More 30% aq hydrogen peroxide (0.15 mL) was added, and stirring was continued for 2 additional days. The volatiles were removed in vacuo. The residue was washed with EtOAc to afford 3-methyl-1H-pyrido[3,4-b]pyrazin-2-one (0.8 g) as a yellowish solid. 0.7 g of this material and PyBroP (2.11 g) were suspended in DMF (3 mL). DIPEA (1.16 mL) was added and the mixture was stirred at ambient temperature overnight. The precipitated solid was filtered off, washed with ethanol, and dried to afford 2-(benzotriazol-1-yloxy)-3-methyl-pyrido[3,4-b]pyrazine (0.7 g) as a white solid. 430 mg of this material was suspended in ethanol (13 mL) and treated with hydrazine hydrate (0.5 mL) at 85° C. for 20 min. The solid was filtered off, washed with ethanol, and dried to afford IId (180 mg) as a yellowish solid sufficiently pure for the next step.

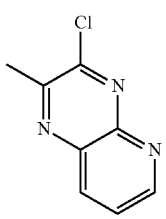

3-Chloro-2-methyl-pyrido[2,3-b]pyrazine (IIId). Ethyl pyruvate (1.22 mL) was dissolved in methanol (10 mL) and added to a cold solution of 2,3-diaminopyridine (1.09 g) in methanol MeOH (20 mL) and the mixture was stirred at ambient temperature. The solid was filtered off and washed with cold methanol to afford 2-methyl-4H-pyrido[2,3-b]pyrazin-3-one (1.1 g) as a grey solid. 1.0 g of this material was suspended in acetonitrile (10 mL) and phosphoryl chloride (1.16 mL) was added. The mixture was heated at 120° C. for 0.5 h under MW conditions. The crude mixture was partitioned between water and EtOAc. The organic layer was washed with brine, dried over Na₂SO₄, filtered, and concentrated in vacuo to afford IIId (460 mg) as a red solid sufficiently pure for the next step.

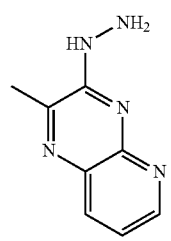

IId (2-Methyl-pyrido[2,3-b]pyrazin-3-yl)-hydrazine (IId). A mixture of IIId (0.61 g) and hydrazine hydrate (0.5 mL) in ethanol (5 mL) was stirred at room temperature for 10 min. The precipitated white solid was filtered off, and washed with ethanol and dried to afford IId (0.43 g) sufficiently pure for the next step.

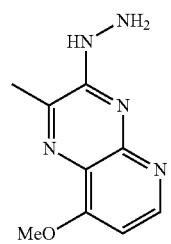

IIe (8-Methoxy-2-methyl-pyrido[2,3-b]pyrazin-3-yl)-hydrazine (IIe). To a solution of 4-chloro-pyridin-2-ylamine (5 g) in 96% aq H₂SO₄ (20 mL) at 0° C. was added a mixture solution of 70% aq HNO₃ (2.5 mL) and 96% aq H₂SO₄ (10 mL) drop-wise. After the addition was completed, the mixture was stirred at room temperature for 2 h. The solution was poured onto ice/water and 6M aq. NaOH was added drop-wise to adjust pH to 9. Then the solid was filtered off, washed with water, and dried before it was purified by chromatography on alumina (eluent: pentane:EtOAc 2:1) to afford 4-chloro-3-nitro-pyridin-2-ylamine (1.2 g). 200 mg of this material was dissolved methanol (3 mL) and NaOMe (125 mg) was added before the mixture was stirred at 60° C. for 16 h. 37% aq HCl was added drop-wise to adjust pH to 6. The mixture was cooled to 0° C., and the precipitated solid was filtered off, washed with water, and dried to afford 4-methoxy-3-nitro-pyridin-2-ylamine (180 mg). This material was dissolved in methanol (20 mL) and treated with hydrogen gas (1 bar) in the presence of 10% palladium on charcoal at room temperature for 2 h. The mixture was filtered and the filtrate was concentrated in vacuo to afford 4-methoxy-pyridine-2,3-diamine (50 mg). This procedure was repeated to produce more material. In the next step, 4-methoxy-pyridine-2,3-diamine (6.8 g) was dissolved in ethanol (200 mL). To this solution was slowly added methyl pyruvate (4.9 mL) at room temperature, and the mixture was stirred at ambient temperature for 3 h before the volatiles were removed in vacuo. The residue was purified by chromatography on silica gel (eluent: pentane:EtOAc 5:1 to 0:1) to give afford 8-methoxy-2-methyl-4H-pyrido[2,3-b]pyrazin-3-one (6.1 g). To a suspension of 3 g of this material in DMF (12 mL) was added PyBroP (7.65 g) followed by DBU (3.58 g). The mixture was stirred overnight before the precipitated solid was filtered off, washed with ethanol, and dried to afford 3-(benzotriazol-1-yloxy)-8-methoxy-2-methyl-pyrido[2,3-b]pyrazine (3.5 g). 1.5 g of this material was dissolved in a mixture of ethanol (10 mL) and DCM (60 mL). Hydrazine monohydrate (3.6 g) was added, and the mixture was stirred overnight at ambient temperature before the volatiles were removed in vacuo. The residual solid was triturated from ethanol, filtered off, washed with ethanol, and dried to afford (8-methoxy-2-methyl-pyrido[2,3-b]pyrazin-3-yl)-hydrazine IIe (0.9 g).

COMPOUNDS OF THE INVENTION

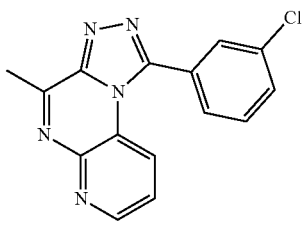

Ia1

Example Ia1

1-(3-Chloro-phenyl)-4-methyl-2,3,5,6,9b-pentaaza-cyclopenta[a]naphthalene. A mixture of IIa (100 mg), PyBroP (277 mg), 3-chloro-benzoic acid (88.9 mg), and DIPEA (0.3 mL) in DMF (10 mL) was stirred at ambient temperature for 16 h. The volatiles were removed in vacuo. The residue was stirred in DCM (5 mL) to precipitate the corresponding hydrazide (150 mg). This material was suspended for 5 min at ambient temperature in a mixture of acetonitrile (10 mL) and DIPEA (0.4 mL). PhPOCl₂ (0.13 mL) was added, and the mixture was stirred at ambient temperature and became homogeneous. Stirring was continued until a white solid precipitated. This material was filtered off, washed with acetonitrile, and dried. This material (140 mg) was dissolved in methanol (10 mL) and was treated with Na₂CO₃ (10 mg) at ambient temperature for 0.5 h. Then the volume was reduced approximately 50% in a flask open to air. The precipitated solid was filtered off and dried to afford example Ia1 (60 mg). LC/MS (method 132): RT(PDA)=1.59 min; PDA/ELS-purities 100%/100%; mass observed 296.1.

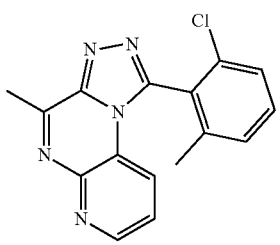

Ia2

Example Ia2

1-(2-Chloro-6-methyl-phenyl)-4-methyl-2,3,5,6,9b-pentaaza-cyclopenta[a]naphthalene. A mixture of IIa (90 mg), PyBroP (264 mg), 2-chloro-6-methyl benzoyl chloride (87 mg), and DIPEA (0.7 mL) was stirred in DMF (2 mL) at ambient temperature for 2 days. The volatiles were removed in vacuo. The residue was purified by preparative TLC (eluent: DCM/methanol 20/1) to afford the corresponding hydrazide (80 mg). A larger portion of this material (100 mg) prepared in a similar manner was dissolved in a mixture of acetonitrile (5 mL) and DIPEA (0.42 mL) and treated with PhPOCl$_2$ (0.08 mL) for 5 min at ambient temperature. The volatiles were removed in vacuo. The residue was purified by preparative TLC (eluent: DCM/methanol 20/1) to afford example Ia2 (85 mg). LC/MS (method 132): RT(PDA)=1.55 min; PDA/ELS-purities 97.8%/100%; mass observed 310.1.

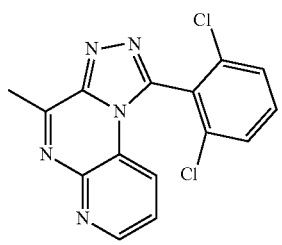

Example Ia3

1-(2,6-Dichloro-phenyl)-4-methyl-2,3,5,6,9b-pentaaza-cyclopenta[a]naphthalene. A mixture of IIa (80 mg), PyBroP (221 mg), 2,6-dichloro-benzoic acid (87 mg), and DIPEA (0.2 mL) was stirred at ambient temperature in DMF for 2 days. The volatiles were removed in vacuo. The residue was purified by preparative TLC (eluent: DCM/methanol 20/1) to give the corresponding hydrazide (100 mg). This material was suspended in acetonitrile (3 mL) and treated with DIPEA (0.5 mL) and PhPOCl$_2$ (0.08 mL) for 5 min at ambient temperature. The volatiles were removed in vacuo. The residue was purified by preparative TLC (eluent: DCM/methanol 20/1) to afford example Ia3 (15 mg). LC/MS (method 131): RT(PDA)=1.07 min; PDA/ELS-purities 96.1%/100%; mass observed 330.1.

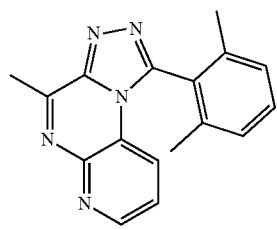

Example Ia4

1-(2,6-Dimethyl-phenyl)-4-methyl-2,3,5,6,9b-pentaaza-cyclopenta[a]naphthalene. To a mixture of IIa (100 mg), DIPEA (0.2 mL) in DMF (2 mL) was added 2,6-dimethyl benzoyl chloride (96 mg), and the mixture was stirred at ambient temperature for 5 min. The volatiles were removed in vacuo. The residue was purified by preparative TLC (eluent: DCM/methanol 20/1) to give the corresponding hydrazide (114 mg). 45 mg of this material was suspended in acetonitrile (2 mL) and treated with DIPEA (0.2 mL) for 5 min and then with PhPOCl$_2$ (0.11 mL). The mixture was purified directly by preparative TLC (eluent: pentane/EtOAc 1/1) to afford example Ia4 (7.2 mg). LC/MS (method 132): RT(PDA) =1.54 min; PDA/ELS-purities 98.0%/100%; mass observed 290.0.

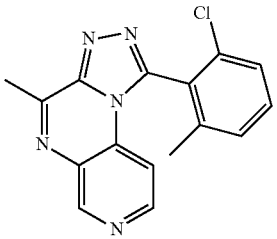

Example Ib1

1-(2-Chloro-phenyl)-4-methyl-2,3,5,7,9b-pentaaza-cyclopenta[a]naphthalene. A mixture of IIb (480 mg,) 2-chloro benzoic acid (430 mg), and PyBroP (1.33 g) was suspended in DMF (12 mL), and DIPEA (0.97 mL) was added. The mixture stirred overnight. The volatiles were removed in vacuo. The residue was suspended in DCM. The solid was filtered off, washed with DCM, and dried to afford 2-chloro-benzoic acid N'-(3-methyl-pyrido[3,4-b]pyrazin-2-yl)-hydrazide (400 mg) as a yellow sold. This material was suspended in acetonitrile (30 mL) at 0° C. DIPEA (1.7 mL) and PhPOCl$_2$ (0.35 mL) were added. The mixture was stirred at 0° C. for 0.5 h before it was allowed to warm to ambient temperature and stirred for 10 min. Most of the volatiles were removed in vacuo. The solid was filtered off, washed with acetonitrile, and dried to afford a solid (0.3 g). This material was dissolved in methanol (30 mL) and treated with Na$_2$CO$_3$ (100 mg) at ambient temperature for 1 h. The solid was filtered off, and the residue was concentrated in vacuo. The residue was purified by preparative TLC (eluent: DCM/methanol 10:1) to afford example Ib1 (180 mg) as a white solid. LC/MS (method 132): RT(PDA)=1.54 min; PDA/ELS-purities 99.0%/100%; mass observed 296.1.

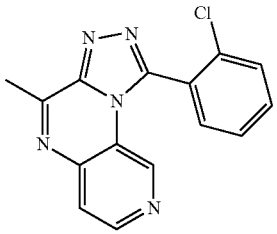

Example Ic1

1-(2-Chloro-phenyl)-4-methyl-2,3,5,8,9b-pentaaza-cyclopenta[a]naphthalene. A mixture of IIc (200 mg), 2-chloro benzoic acid (179 mg), and PyBroP (554 mg) was suspended in DMF (7 mL). DIPEA (0.41 mL) was added, and the mixture was stirred at ambient temperature. The volatiles were removed in vacuo. The residue was suspended in DCM. The solid was filtered off, washed with DCM, and dried to afford 2-chloro-benzoic acid N'-(2-methyl-pyrido[3,4-b]pyrazin-3-yl)-hydrazide (313 mg) as a yellow sold. 250 mg of this material was suspended in acetonitrile (200 mL) and treated with DIPEA (1.1 mL) and PhPOCl$_2$ (0.22 mL) at 0° C. After 10 min, the mixture was allowed to warm to ambient temperature and stirred for another 5 min. Most of the volatiles were removed in vacuo. The solid was filtered off, washed with acetonitrile, and dried. This material (0.32 g) was dissolved in a mixture of methanol (100 mL) and acetonitrile (20 mL). Na$_2$CO$_3$ (30 mg) and a few drops of water were added, and the mixture was stirred at ambient temperature for 0.5 h. The solid was filtered off. The filtrate was concentrated in vacuo. The residue was purified by preparative TLC (eluent: DCM/methanol 10:1) to afford example Ic1 (162 mg) as a white solid. LC/MS (method 132): RT(PDA)=1.58 min; PDA/ELS-purities 94.0%/100%; mass observed 296.1.

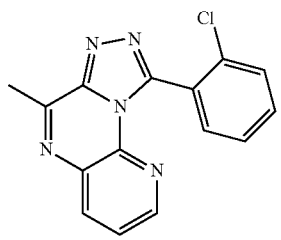

Example Id1

1-(2-Chloro-phenyl)-4-methyl-2,3,5,9,9b-pentaaza-cyclopenta[a]naphthalene. IIId (450 mg) was dissolved in acetonitrile (10 mL) and the solution was flushed with nitrogen before 2-chlorobenzhydrazide (0.44 g) was added. The mixture was heated at 150° C. for 0.5 h under MW conditions. The crude mixture was partitioned between water and EtOAc and basified with NaHCO$_3$. The solid was filtered off, and the organic part of the filtrate washed with brine, dried over MgSO$_4$, filtered, and concentrated in vacuo. The residue was purified by chromatography on silica (eluent 1:1 heptanes/EtOAc→EtOAc) to afford a sticky solid. This material was suspended in a 10:1 mixture of diethyl ether and EtOAc, and the solid was filtered off and dried to afford example Id1 (82 mg). LC/MS (method 131): RT(PDA)=1.33 min; PDA/ELS-purities 97.1%/100%; mass observed 296.2.

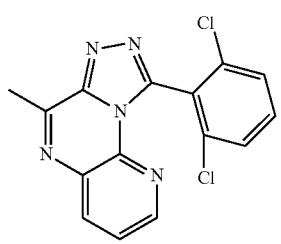

Example Id2

1-(2,6-Dichloro-phenyl)-4-methyl-2,3,5,9,9b-pentaaza-cyclopenta[a]naphthalene. Prepared as described for example Id3 using IId (100 mg) and 2,6-dichloro benzoyl chloride (118 mg) to obtain the corresponding hydrazide (170 mg) that was converted to example Id2 (18 mg). LC/MS (method 132): RT(PDA)=1.77 min; PDA/ELS purities 99.0%/100%; mass observed 330.1.

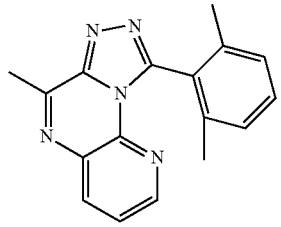

Example Id3

1-(2,6-Dimethyl-phenyl)-4-methyl-2,3,5,9,9b-pentaaza-cyclopenta[a]naphthalene. To a mixture of IId (50 mg), DIPEA (0.2 mL) in DMF (2 mL) was added 2,6-dimethyl benzoyl chloride (48 mg), and the mixture was stirred for 5 min at ambient temperature. The volatiles were removed in vacuo. The residue was purified by preparative TLC (eluent: DCM/methanol 20/1) to afford the corresponding hydrazide (45 mg). This material was mixed with acetonitrile (2 mL) and DIPEA (0.2 mL) and treated with PhPOCl$_2$ (0.04 mL) for 3 min at ambient temperature. The volatiles were removed in vacuo. The residue was purified by preparative TLC (eluent: DCM/methanol 30/1) to afford example Id3 (12 mg). LC/MS (method 132): RT(PDA)=1.78 min; PDA purity 100%; mass observed 290.0.

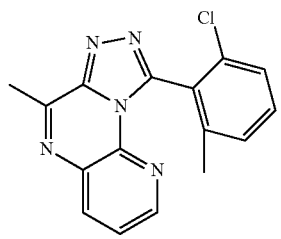

Example Id4

1-(2-Chloro-6-methyl-phenyl)-4-methyl-2,3,5,9,9b-pentaaza-cyclopenta[a]naphthalene. IId (90 mg) and DIPEA (0.4 mL) were dissolved in DMF, and 2-chloro-6-methyl benzoyl chloride (106 mg) was added. The mixture was stirred at ambient temperature for 5 min. The volatiles were removed in vacuo. The residue was purified by preparative TLC (eluent: DCM/methanol 20:1) to afford 2-chloro-6-methyl-benzoic acid N'-(2-methyl-pyrido[2,3-b]pyrazin-3-yl)-hydrazide (110 mg). This material and DIPEA (0.24 mL) were mixed in acetonitrile (2 mL) and treated with PhPOCl$_2$ (0.1 mL) for 5 min at ambient temperature. The volatiles were removed in vacuo. The residue was purified by preparative TLC (eluent: pentane/EtOAc 1:3) to afford example Id4 (60 mg). LC/MS (method 132): RT(PDA)=1.79 min; PDA/ELS purities 98.4%/100%; mass observed 310.3.

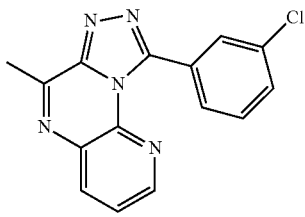

Example Ic5

1-(3-Chloro-phenyl)-4-methyl-2,3,5,9,9b-pentaaza-cyclopenta[a]naphthalene. Prepared as described for example Id4 using IId (200 mg) and 3-chloro-benzoyl chloride (200 mg) to afford the corresponding hydrazine (130 mg). This material was suspended in acetonitrile (10 mL) and treated with DIPEA (0.4 mL) and PhPOCl₂ (0.11 mL) until the mixture became homogenous and subsequently a white solid precipitated. This material was filtered off, washed with acetonitrile, and dried. The dried material (170 mg) was dissolved in methanol (20 mL) and treated with Na₂CO₃ (10 mg) at ambient temperature for 2 h. The volatiles were removed in vacuo. The residue was purified by preparative TLC (eluent: DCM/methanol 20:1) to afford example Id5 (31.2 mg). LC/MS (method 132): RT(PDA)=1.88 min; PDA/ELS purities 99.6%/100%; mass observed 296.2.

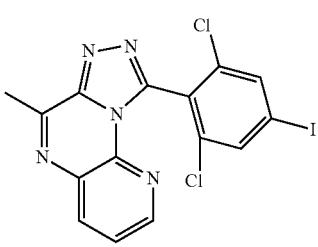

Example Id6

1-(2,6-Dichloro-4-iodo-phenyl)-4-methyl-2,3,5,9,9b-pentaaza-cyclopenta[a]naphthalene. 4-Amino-2,6-dichloro-phenol (50 g) was treated with Boc₂O (69 g) in 1,4-dioxane (0.8 L) at reflux for 18 h before the volatiles were removed in vacuo affording (3,5-dichloro-4-hydroxy-phenyl)-carbamic acid tert-butyl ester (70 g), which was used for next step without further purification. This procedure was repeated to afford more of this material. 86 g of the compound and 2,6-dimethylpyridine (49 g) were dissolved in DCM (0.9 L). Tf₂O (104 g) was added drop-wise at −78° C. The mixture was allowed to warm to room temperature whereafter it was stirred for 2 h. The crude mixture was partitioned between water and DCM. The organic layer was dried over Na₂SO₄, filtered, and concentrated in vacuo. The residue was purified by column chromatography on silica gel (eluent: petane:EtOAc 30:1) to afford trifluoro-methanesulfonic acid 4-tert-butoxycarbonylamino-2,6-dichloro-phenyl ester (73 g). This material was mixed with Pd(DPPF)Cl₂ (4 g), triethylamine (102 mL) in a mixture of methanol (580 mL) and DMF (384 mL). The mixture was refluxed under an atmosphere of carbon monoxide overnight before it was cooled, concentrated in vacuo. The residue was partitioned between water and EtOAc. The organic layer was washed with brine, dried over Na₂SO₄, filtered, and concentrated in vacuo. The residue was purified by column chromatography on silica gel (eluent: pentane:EtOAc 80:1) to afford 4-tert-butoxycarbonylamino-2,6-dichloro-benzoic acid methyl ester (12 g). 7 g of this material was dissolved in 37% aq HCl (70 mL), and a solution of sodium nitrite (3.75 g) in water (100 mL) was added drop-wise at 0° C. The mixture was stirred for 30 min at 0° C. before it was filtered and the filtrate was added to a pre-cooled solution of potassium iodide (24 g) at 0° C. The mixture was warmed to room temperature and stirred overnight. The mixture was extracted with EtOAc. The organic layer was washed with sat. aq NaHSO₃ before it was dried over Na₂SO₄, filtered, and concentrated in vacuo. The residue was purified by column chromatography on silica gel (eluent: pentane:EtOAc 50:1) to afford 2,6-dichloro-4-iodo-benzoic acid methyl ester (7.9 g). This material was dissolved in a mixture of pyridine (40 mL) and water (7 mL) and treated with lithium iodide (3.2 g) at 130° C. for 30 h before the volatiles were removed in vacuo. The residue was partitioned between 2M aq HCl and EtOAc. The organic layer was concentrated in vacuo to afford 2,6-dichloro-4-iodo-benzoic acid (3 g). 0.5 g of this material was stirred in thionyl chloride (8 mL) at 60° C. for 3 h before excess thionyl chloride was removed in vacuo. The residue was washed with ether and dried to afford 2,6-dichloro-4-iodo-benzoyl chloride (0.53 g) that was used directly in the next step where it was dissolved in a mixture of DMF (20 mL) and DIPEA (0.57 mL). To this solution was added IId (277 mg). The mixture was stirred at room temperature for 1 h. The volatiles were removed in vacuo, and residue was purified by chromatography on silica gel (eluent: DCM:MeOH 100:1 to 30:1) to afford 2,6-dichloro-4-iodo-benzoic acid N'-(2-methyl-pyrido[2,3-b]pyrazin-3-yl)-hydrazide (250 mg). This procedure was repeated to afford more material. 380 mg of the compound was dissolved in 1,4-dioxane (5 mL). Phosphoryl chloride (4 mL) was added, and the mixture was stirred at 90° C. for 1.5 h. The volatiles were removed in vacuo. The residue was partitioned between DCM and water. The organic layer was washed with sat. aq. NaHCO₃, dried over NaSO₄, filtered, and concentrated in vacuo. The residue was purified by preparative TLC (eluent: pentane:EtOAc 2:1) to afford example Id6 (45.5 mg). LC/MS (method WXE-AB10): RT(PDA)=2.39 min; PDA/ELS purities 97.1%/98.3%; mass observed 456.0.

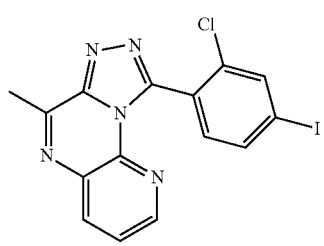

Example Id7

1-(2-Chloro-4-iodo-phenyl)-4-methyl-2,3,5,9,9b-pentaaza-cyclopenta[a]naphthalene. A mixture of 2-chloro-4-iodo-benzoic acid (470 mg) in thionyl chloride (6 mL) was stirred at 60° C. for 3 h. The excess thionyl chloride was removed in vacuo. The residue was washed with ether and dried to afford 2-chloro-4-iodo-benzoyl chloride (0.5 g), which was used directly in the next step where it was dissolved in 1,4-dioxane (10 mL). Phosphoryl chloride (5 mL) and IId (246 mg) were added, and the mixture was stirred at 90° C. for 1.5 h. The volatiles were removed in vacuo. The residue was partitioned between water and DCM. The organic layer was washed with sat. aq. NaHCO$_3$, dried over NaSO$_4$, filtered, and concentrated in vacuo. The residue was purified by column chromatography on silica gel (eluent: pentane: EtOAc 10:1 to 5:1) to afford example Id7 (250 mg). LC/MS (method WXE-AB10): RT(PDA)=2.26 min; PDA/ELS purities 99%/99%; mass observed 422.0.

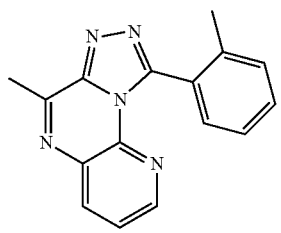

Example Id8

1-(2-Methyl-phenyl)-4-methyl-2,3,5,9,9b-pentaaza-cyclopenta[a]naphthalene. IId (400 mg) was dissolved in a mixture of DIPEA (0.8 mL) and DMF (8 mL). 2-Methyl-benzoyl chloride (368 mg) was added, and the mixture was stirred for 0.5 h at ambient temperature before the volatiles were removed in vacuo. The residue was purified by preparative TLC (eluent: DCM:MeOH 25:1) to afford 2-methyl-benzoic acid N'-(2-methyl-pyrido[2,3-b]pyrazin-3-yl)-hydrazide (310 mg). 100 mg of this material was dissolved in acetonitrile (2 mL), and DIPEA (0.24 mL) and PhP(O)Cl$_2$ (0.07 mL) were added. The mixture was stirred at ambient temperature for 15 min before the crude mixture was purified by preparative TLC (eluent: EtOAc:pentane 3:2) to afford example Id8 (5 mg). LC/MS (method WXE-AB01): RT(PDA)=2.05 min; PDA/ELS purities 95.3%/95.7%; mass observed 276.2.

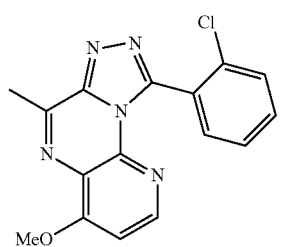

Example Ie1

1-(2-Chloro-phenyl)-6-methoxy-4-methyl-2,3,5,9,9b-pentaaza-cyclopenta[a]naphthalene. To a suspension of IIe (500 mg) in DCM (80 mL) was added compound 2-chlorobenzaldehyde (377 mg). The mixture was stirred at 40° C. for two days before the volatiles were removed in vacuo. The residue was purified by chromatography on silica gel (eluent: pentane/EtOAc from 1:0 to 0:1) to afford N-[1-(2-chlorophenyl)-methylidene]-N'-(8-methoxy-2-methyl-pyrido[2,3-b]pyrazin-3-yl)-hydrazine (0.5 g). This material was dissolved in DCM (60 mL) and (bisacethoxy)iodobenzene (540 mg) was added, and the reaction solution was stirred at room temperature overnight. The volatiles were removed in vacuo, and the residue was purified by chromatography on silica gel (eluent: pentane/EtOAc from 1:0 to 0:1) to afford example Ie1 (100 mg). LC/MS (method 550): RT(PDA)=0.55 min; PDA/ELS purities 90%/100%; mass observed 326.0.

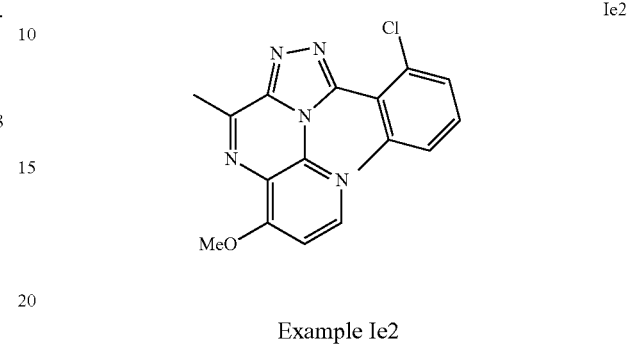

Example Ie2

1-(2-Chloro-6-methyl-phenyl)-6-methoxy-4-methyl-2,3,5,9,9b-pentaaza-cyclopenta[a]naphthalene. To a suspension of IIe (0.5 g) in DCM (80 mL) was added 2-chloro-6-methyl-benzaldehyde compound (377 mg). The mixture was stirred at 40° C. for two days before (bisacetoxy)iodobenzene (864 mg) was added and stirring was continued for overnight at ambient temperature. The volatiles were removed in vacuo, and the residue was purified by preparative TLC (eluent: EtOAc) to afford example Ie2 (185 mg). LC/MS (method WXE-AB01): RT(PDA)=1.9 min; PDA/ELS purities 100%/100%; mass observed 340.1.

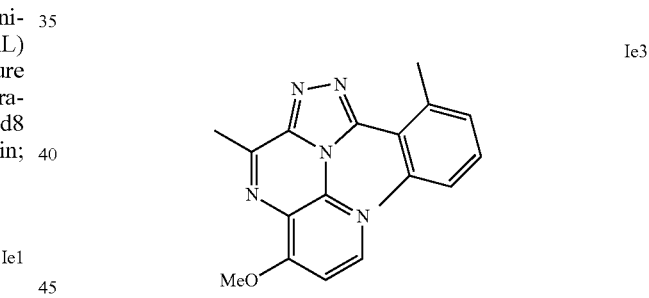

Example Ie3

1-(2,6-Bismethyl-phenyl)-6-methoxy-4-methyl-2,3,5,9,9b-pentaaza-cyclopenta[a]naphthalene. To a suspension of IIe (0.5 g) in DCM (80 mL) was added 2,6-bismethyl-benzaldehyde (377 mg), and the mixture was stirred at 40° C. for two days before (bisacetoxy)iodobenzene (864 mg) was added and the mixture was stirred at ambient temperature overnight. The volatiles were removed in vacuo, and the residue was purified by chromatography on silica gel (eluent: EtOAc) to afford example Ie3 (175 mg). LC/MS (method WXE-AB10): RT(PDA)=1.88 min; PDA/ELS purities 100%/100%; mass observed 320.1.

PDE In-Vitro Assays

The inhibitory activities of the compound of the invention were determined in connection with the following methods:

PDE10A Enzyme

Active PDE10A enzyme is prepared in a number of ways for use in PDE assays (Loughney, K. et al. Gene 1999, 234, 109-117; Fujishige, K. et al. Eur J. Biochem. 1999, 266, 1118-1127 and Soderling, S. et al. Proc. Natl. Acad. Sci. 1999, 96, 7071-7076). PDE10A can be expressed as full-length proteins or as truncated proteins, as long as they express the catalytic domain. PDE10A can be prepared in different cell types, for example insect cells or *E. coli*. An example of a method to obtain catalytically active PDE10A is as follows: The catalytic domain of human PDE10A (amino acids 440-779 from the sequence with accession number NP 006652) is amplified from total human brain total RNA by standard RT-PCR and is cloned into the BamH1 and XhoI sites of the pET28a vector (Novagen). Expression in coli is performed according to standard protocols. Briefly, the expression plasmids are transformed into the BL21(DE3) *E. coli* strain, and 50 mL cultures inoculated with the cells allowed to grow to an OD600 of 0.4-0.6 before protein expression is induced with 0.5 mM IPTG. Following induction, the cells are incubated overnight at room temperature, after which the cells are collected by centrifugation. Cells expressing PDE10A are resuspended in 12 mL (50 mM TRIS-HCl-pH8.0, 1 mM $MgCl_2$ and protease inhibitors). The cells are lysed by sonication, and after all cells are lysed, TritonX100 is added according to Novagen protocols. PDE10A is partially purified on Q sepharose and the most active fractions were pooled.

PDE10A Inhibition Assay

A typical PDE10A assay was performed as follows: the assay was performed in 60 μL samples containing a fixed amount of the PDE2A enzyme (sufficient to convert 20-25% of the cyclic nucleotide substrate), a buffer (50 mM HEPES pH 7.6; 10 mM $MgCl_2$; 0.02% Tween20), 10 nM tritium labelled cAMP and varying amounts of inhibitors. Reactions were initiated by addition of the cyclic nucleotide substrate, and reactions were allowed to proceed for 1 h at room temperature before being terminated through mixing with 20 μL (0.2 mg) yttrium silicate SPA beads (Amersham). The beads were allowed to settle for 1 h in the dark before the plates were counted in a Wallac 1450 Microbeta counter. The measured signals were converted to activity relative to an uninhibited control (100%) and $IC_{50}$ values were calculated using XlFit (model 205, IDBS).

PDE2A Enzyme

Likewise, active human PDE2A enzyme (ATCC68585) is prepared in a number of ways for use in PDE assays and procedures are well known to those skilled in the art.

PDE2A Inhibition Assay

A typical PDE2A assay was performed as follows: the assay was performed in 60 μL samples containing a fixed amount of the PDE2A enzyme (sufficient to convert 20-25% of the cyclic nucleotide substrate), a buffer (50 mM HEPES pH 7.6; 10 mM $MgCl_2$; 0.02% Tween20), 0.1 mg/ml BSA, 15 nM tritium labelled cAMP and varying amounts of inhibitors. Reactions were initiated by addition of the cyclic nucleotide substrate, and reactions were allowed to proceed for 1 h at room temperature before being terminated through mixing with 20 μL (0.2 mg) yttrium silicate SPA beads (Amersham). The beads were allowed to settle for 1 h in the dark before the plates were counted in a Wallac 1450 Microbeta counter. The measured signals were converted to activity relative to an uninhibited control (100%) and $IC_{50}$ values were calculated using XlFit (model 205, IDBS).

Data obtained for selected examples are listed in the table below.

| | PDE2A $IC_{50}$ | PDE10 $IC_{50}$ |
|---|---|---|
| Example Ia2 | 504 nM | 48% inhibition @ 10,000 nM |
| Example Ib1 | 471 nM | 68% inhibition @ 10,000 nM |
| Example Ic1 | 69 nM | 1762 nM |

The invention claimed is:

1. A compound of Formula I:

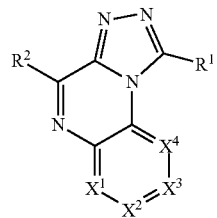

Formula I wherein each $X^1$, $X^2$, and $X^3$ is independently $CR^3$ and $X^4$ is N;

wherein $R^1$ is $C_1$-$C_6$ alkyl, $C_3$-$C_6$ cycloalkyl, tetrahydropyranyl, benzyl, phenyl and pyridyl, in which the benzyl, phenyl and pyridyl is optionally substituted with one or more halogen, CN, $C_1$-$C_4$ alkyl, $C_1$-$C_4$ fluoroalkyl, $C_1$-$C_4$ alkoxy, or $C_1$-$C_4$ fluoroalkoxy;

wherein $R^2$ is $C_1$-$C_4$ alkyl or $C_3$-$C_6$ cycloalkyl; and wherein $R^3$ is hydrogen, halogen, CN, —$CO_2H$, —$CONH_2$, —$CON(C_1$-$C_4$ alkyl$)_2$, CHO, $C_1$-$C_4$ alkyl, $C_1$-$C_4$ fluoroalkyl, a cyclic amino containing heterocycle, $C_2$-$C_4$ alkenyl, $C_2$-$C_4$ alkynyl, $C_1$-$C_4$ alkoxy, or $C_1$-$C_4$ fluoroalkoxy; or a pharmaceutically acceptable salt thereof.

2. The compound of claim 1, wherein $R^2$ is $C_1$-$C_4$ alkyl.

3. The compound of claim 1 or 2, wherein $R^2$ is methyl.

4. The compound of claim 1, wherein $R^2$ is $C_3$-$C_6$ cycloalkyl.

5. The compound of claim 1, wherein $R^1$ is $C_1$-$C_4$ alkyl.

6. The compound of claim 1, wherein $R^1$ is $C_3$-$C_6$ cycloalkyl.

7. The compound of claim 1, wherein $R^1$ is tetrahydropyranyl.

8. The compound of claim 1, wherein $R^1$ is benzyl optionally substituted with one or two F, Cl or $C_1$-$C_3$ alkyl.

9. The compound of claim 1, wherein $R^1$ is phenyl optionally substituted with one or two F, Cl or $C_1$-$C_3$ alkyl.

10. The compound of claim 1, wherein $R^1$ is pyridyl optionally substituted with one or two F, Cl or $C_1$-$C_3$ alkyl.

11. The compound of claim 1, wherein $R^1$ is phenyl substituted with one or two F, Cl or $C_1$-$C_3$ alkyl.

12. The compound of claim 1, wherein $R^3$ is hydrogen.

13. The compound of claim 1, wherein $R^3$ is halogen or CHO.

14. The compound of claim 1, wherein $R^3$ is $C_1$-$C_4$ alkyl or $C_1$-$C_4$ alkoxy.

15. The compound of claim 1, wherein $R^3$ is $C_2$-$C_4$ alkenyl or $C_2$-$C_4$ alkynyl.

16. The compound of claim 1, wherein $R^3$ is a cyclic amino containing heterocycle.

17. The compound of claim 1, wherein the compound is 1-(2-Chloro-phenyl)-4-methyl-2,3,5,9,9b-pentaaza-cyclopenta[a]naphthalene.

18. The compound of claim 1, wherein the compound is 1-(2,6-Dichloro-phenyl)-4-methyl-2,3,5,9,9b-pentaaza-cyclopenta[a]naphthalene.

19. The compound of claim 1, wherein the compound is 1-(2,6-Dimethyl-phenyl)-4-methyl-2,3,5,9,9b-pentaaza-cyclopenta[a]naphthalene.

20. The compound of claim 1, wherein in the compound is 1-(2-Chloro-6-methyl-phenyl)-4-methyl-2,3,5,9,9b-pentaaza-cyclopenta[a]naphthalene.

21. The compound of claim 1, wherein the compound is 1-(2-Chloro-phenyl)-6-methoxy-4-methyl-2,3,5,9,9b-pentaaza-cyclopenta[a]naphthalene.

22. The compound of claim 1, wherein the compound is 1-(3-Chloro-phenyl)-4-methyl-2,3,5,9,9b-pentaaza-cyclopenta[a]naphthalene.

23. A pharmaceutical composition comprising the compound of claim 1 or a pharmaceutically acceptable salt thereof and a pharmaceutically acceptable carrier.

* * * * *